United States Patent
Nobori et al.

(12)
(10) Patent No.: US 6,177,593 B1
(45) Date of Patent: Jan. 23, 2001

(54) [TRIS(DIMETHYLAMINO)PHOSPHONIOAMINO]TRIS[TRIS(DIMETHYLAMINO)PHOSPHORANYLIDENEAMINO]PHOSPHONIUM DICHLORIDE AND PREPARATION PROCESS THEREOF

(75) Inventors: Tadahito Nobori; Takaomi Hayashi; Katsuhiko Funaki; Atsushi Shibahara; Isao Hara; Shinji Kiyono; Kazumi Mizutani; Usaji Takaki, all of Kanagawa (JP)

(73) Assignee: Mitsui Chemicals, Inc. (JP)

( * ) Notice: Under 35 U.S.C. 154(b), the term of this patent shall be extended for 0 days.

(21) Appl. No.: 09/216,864

(22) Filed: Dec. 21, 1998

(30) Foreign Application Priority Data

Dec. 22, 1997 (JP) .................................. 9-352932

(51) Int. Cl.⁷ .................. C07F 9/02; C07F 9/06
(52) U.S. Cl. .................................. 564/12
(58) Field of Search .................................. 564/12

(56) References Cited

FOREIGN PATENT DOCUMENTS 0 691 334   1/1996   (EP) .
0 791 600   8/1997   (EP) .

OTHER PUBLICATIONS

Chemical Abstracts; vol. 130; Columbus, Ohio; Abstract No. 110404; Noboru et al; "Preparation of phosphazenium halides and aminotris(amino)phosphonium halides from phosphorous pentahalide and iminotris(amino)phosphoranes", 1999.

Primary Examiner—Shailendra Kumar
(74) Attorney, Agent, or Firm—Burns, Doane, Swecker & Mathis, L.L.P.

(57) ABSTRACT

The compound [tris(dimethylamino)phosphonioamino]tris[tris(dimethylamino)phosphoranylideneamino]phosphonium dichloride can be prepared by contacting hydrogen chloride with tetrakis[tris(dimethylamino)phosphoranylideneamino]phosphonium chloride. The phosphonium dichloride compound can be used in a process wherein it is brought into contact with an OH⁻-form ion exchange resin to prepare tetrakis[tris(dimethylamino)phosphoranylideneamino]phosphonium hydroxide. Separate processes for separating or isolating the phosphonium chloride compound or isolating the phosphonium hydroxide compound from feed solutions wherein an extraction step is used are also set forth.

22 Claims, 3 Drawing Sheets

[TRIS(DIMETHYLAMINO) PHOSPHONIOAMINO]TRIS[TRIS (DIMETHYLAMINO) PHOSPHORANYLIDENEAMINO] PHOSPHONIUM DICHLORIDE AND PREPARATION PROCESS THEREOF

BACKGROUND OF THE INVENTION a) Field of the Invention

This invention relates to novel and useful [tris (dimethylamino)phosphonioamino]tris[tris(dimethylamino) phosphoranylideneamino]phosphonium dichloride.

This compound is extremely useful as a raw material for tetrakis[tris(dimethylamino)phosphoranylideneamino] phosphonium hydroxide which is important as a polymerization catalyst for alkylene oxides.

This [tris(dimethylamino)phosphonioamino]tris[tris (dimethylamino)phosphoranylideneamino]phosphonium dichloride is also an important compound upon extracting tetrakis[tris(dimethylamino)phosphoranylideneamino] phosphonium chloride as its hydrogen chloride addition compound in a water phase from a solution of the chloride in an organic solvent such as a reaction mixture containing the chloride.

Further, the present invention is also concerned with a process for preparing [tris(dimethylamino) phosphonioamino]tris[tris(dimethylamino) phosphoranylideneamino]phosphonium dichloride and also with a process for extracting and separating tetrakis[tris (dimethylamino)phosphoranylideneamino]phosphonium chloride as [tris(dimethylamino)phosphonioamino]tris[tris (dimethylamino)phosphoranylideneamino]phosphonium dichloride, the hydrogen chloride addition compound of the chloride, in a water phase from a solution of the chloride in an organic solvent.

Furthermore, this invention also pertains to a process for preparing tetrakis[tris(dimethylamino) phosphoranylideneamino]phosphonium hydroxide from an aqueous solution of [tris(dimethylamino)phosphonioamino] tris[tris(dimethylamino)phosphoranylideneamino] phosphonium dichloride obtained by conducting extraction and separation as described above and also to a process for isolating the hydroxide as a solid.

Moreover, this invention also relates to a process for regenerating tetrakis[tris(dimethylamino) phosphoranylideneamino]phosphonium chloride from the aqueous solution of the dichloride and isolating the same as a solid.

b) Description of the Related Art

[Tris(dimethylamino)phosphonioamino]tris[tris (dimethylamino)phosphoranylideneamino]phosphonium dichloride is a compound absolutely unknown to date. Further, it has heretofore been totally unknown and undisclosed in any publication that, when tetrakis[tris (dimethylamino)phosphoranylideneamino]phosphonium chloride and hydrogen chloride are brought into contact with each other, [tris(dimethylamino)phosphonioamino]tris[tris (dimethylamino)phosphoranylideneamino]phosphonium dichloride as the hydrogen chloride addition product of the chloride is formed.

Needless to say, there is absolutely no precedent case of practice of the process for extracting and separating tetrakis [tris(dimethylamino)phosphoranylideneamino] phosphonium chloride as [tris(dimethylamino) phosphonioamino]tris[tris(dimethylamino) phosphoranylideneamino]phosphonium dichloride, the hydrogen chloride addition compound of the chloride, in a water phase from a solution of the chloride in an organic solvent, the process for preparing tetrakis[tris (dimethylamino)phosphoranylideneamino]phosphonium hydroxide from an aqueous solution of [tris(dimethylamino) phosphonioamino]tris[tris(dimethylamino) phosphoranylideneamino]phosphonium dichloride obtained by conducting extraction and separation as described above, or the process for isolating the hydroxide as a solid; and no publications suggestive of such processes.

Furthermore, no process is known at all and is suggested in any publication for regenerating tetrakis[tris (dimethylamino)phosphoranylideneamino]phosphonium chloride from the aqueous solution of the dichloride and isolating the same as a solid.

SUMMARY OF THE INVENTION

A first object of the present invention is to provide a raw material which upon preparation of tetrakis[tris (dimethylamino)phosphoranylideneamino]phosphonium hydroxide important as a polymerization catalyst for alkylene oxides, can easily afford the hydroxide by an extremely convenient process.

A second object of the present invention is to provide the convenient preparation process for the raw material.

Tetrakis[tris(dimethylamino)phosphoranylideneamino] phosphonium chloride is an important compound as a raw material for tetrakis[tris(dimethylamino) phosphoranylideneamino]phosphonium hydroxide.

To convert the chloride into tetrakis[tris(dimethylamino) phosphoranylideneamino]phosphonium hydroxide, it is desired to use the chloride in the form of an aqueous solution.

The chloride is usually obtained by a reaction of phosphorus pentachloride and iminotris(dimethylamino) phosphorane in an organic solvent, and is dissolved extremely well in the organic solvent. This has made it practically impossible to transfer the chloride into a water phase by the convenient method, namely extraction in water. It is therefore extremely difficult to separate the chloride by this method.

There is accordingly a long standing desire for the development of an effective separation method.

Namely, a third object of the present invention is to provide an extraction and separation process of tetrakis[tris (dimethylamino)phosphoranylideneamino]phosphonium chloride by conveniently transferring the chloride into a water phase from a solution of the chloride in an organic solvent.

A fourth object of the present invention is to provide a process for conveniently and easily preparing tetrakis[tris (dimethylamino)phosphoranylideneamino]phosphonium hydroxide from an aqueous solution containing the chloride so extracted and separated and also a process for isolating the hydroxide as a solid.

Moreover, a fifth object of the present invention is to provide a process for regenerating and isolating as a solid tetrakis[tris(dimethylamino)phosphoranylideneamino] phosphonium chloride from the aqueous solution containing the chloride so extracted and separated.

The present inventors have proceeded with an extensive investigation to achieve the above-described objects. As a result, a novel compound capable of extremely conveniently and easily affording tetrakis[tris(dimethylamino)

phosphoranylideneamino]phosphonium chloride, namely [tris(dimethylamino)phosphonioamino]tris[tris (dimethylamino)phosphoranylideneamino]phosphonium dichloride has been found and, moreover, a process has also been found for its easy preparation.

Inherently, tetrakis[tris(dimethylamino) phosphoranylideneamino]phosphonium chloride is soluble up to 4 wt. % or so in water. Nevertheless, attempts to extract and separate the chloride from a solution of the chloride in an organic solvent all resulted in failure due to its high solubility in the organic solvent.

It has however been surprisingly found that extraction with an aqueous solution of hydrogen chloride in place of pure water converts the chloride into its hydrogen chloride addition compound, i.e., [tris(dimethylamino) phosphonioamino]tris[tris(dimethylamino) phosphoranylideneamino]phosphonium dichloride, leading to a substantial increase in the solubility in water and also to a significant decrease in the solubility in an organic solvent so that the dichloride can be transferred into a water phase with extremely high efficiency. Here, the organic solvent must be immiscible with water.

It has also been found that the hydrogen chloride addition compound of tetrakis[tris(dimethylamino) phosphoranylideneamino]phosphonium chloride, namely [tris(dimethylamino)phosphonioamino]tris[tris (dimethylamino)phosphoranylideneamino]phosphonium dichloride so extracted and separated can be converted into tetrakis[tris(dimethylamino)phosphoranylideneamino] phosphonium hydroxide by simply bringing its aqueous solution into contact with an OH⁻-form ion exchange resin.

It has also been found that neutralization of an aqueous solution of the dichloride makes it possible to easily regenerate tetrakis[tris(dimethylamino)phosphoranylideneamino] phosphonium chloride. Based on these findings, the present inventors have completed the present invention.

Described specifically, the present invention provides:

[Tris(dimethylamino)phosphonioamino]tris[tris (dimethylamino)phosphoranylideneamino] phosphonium dichloride represented by the following formula (1):

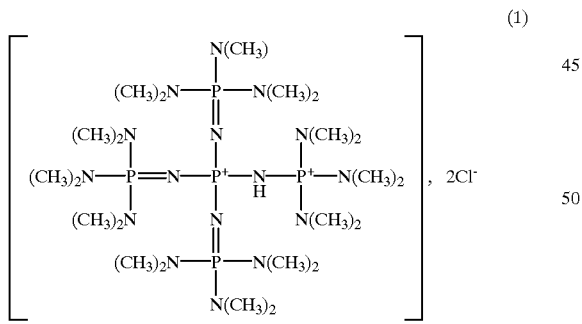

A process for preparing [tris(dimethylamino) phosphonioamino]tris[tris(dimethylamino) phosphoranylideneamino]phosphonium dichloride, which comprises:
  bringing hydrogen chloride into contact with tetrakis[tris (dimethylamino)phosphoranylideneamino] phosphonium chloride, whereby the hydrogen chloride is added on the tetrakis[tris(dimethylamino) phosphoranylideneamino]phosphonium chloride.

A process for separating tetrakis[tris(dimethylamino) phosphoranylideneamino]phosphonium chloride from a feed solution containing at least the tetrakis[tris (dimethylamino)phosphoranylideneamino]phosphonium chloride and a substantially water-immiscible organic solvent, which comprises:
  adding an aqueous solution of hydrogen chloride to the feed solution either after washing the feed solution with water or without washing the same, whereby the tetrakis[tris(dimethylamino)phosphoranylideneamino] phosphonium chloride is extracted out in a water phase as [tris(dimethylamino)phosphonioamino]tris[tris (dimethylamino)phosphoranylideneamino] phosphonium dichloride which is a hydrogen chloride addition compound of the chloride.

A process for preparing tetrakis[tris(dimethylamino) phosphoranylideneamino]phosphonium hydroxide, which comprises:
  adding an aqueous solution of hydrogen chloride to a feed solution, which contains at least the tetrakis[tris (dimethylamino)phosphoranylideneamino] phosphonium chloride and a substantially water-immiscible organic solvent, either after washing the feed solution with water or without washing the same, whereby the tetrakis[tris(dimethylamino) phosphoranylideneamino]phosphonium chloride is extracted out in a water phase as [tris(dimethylamino) phosphonioamino]tris[tris(dimethylamino) phosphoranylideneamino]phosphonium dichloride which is a hydrogen chloride addition compound of the chloride; and then
  bringing the resulting aqueous solution of the [tris (dimethylamino)phosphonioamino]tris[tris (dimethylamino)phosphoranylideneamino] phosphonium dichloride into contact with an OH⁻-form ion exchange resin.

A process for isolating tetrakis[tris(dimethylamino) phosphoranylideneamino]phosphonium hydroxide, which comprises:
  adding an aqueous solution of hydrogen chloride to a feed solution, which contains at least the tetrakis[tris (dimethylamino)phosphoranylideneamino] phosphonium chloride and a substantially water-immiscible organic solvent, either after washing the feed solution with water or without washing the same, whereby the tetrakis[tris(dimethylamino) phosphoranylideneamino]phosphonium chloride is extracted out in a water phase as [tris(dimethylamino) phosphonioamino]tris[tris(dimethylamino) phosphoranylideneamino]phosphonium dichloride which is a hydrogen chloride addition compound of the chloride;
  bringing the resulting aqueous solution of the [tris (dimethylamino)phosphonioamino]tris[tris (dimethylamino)phosphoranylideneamino] phosphonium dichloride into contact with an OH⁻-form ion exchange resin, whereby an aqueous solution of tetrakis[tris(dimethylamino) phosphoranylideneamino]phosphonium hydroxide is obtained; and then
  distilling off water under reduced pressure at a temperature not higher than 80° C. from the aqueous solution of the hydroxide, whereby the tetrakis[tris (dimethylamino)phosphoranylideneamino] phosphonium hydroxide is formed into a solid.

A process for isolating tetrakis[tris(dimethylamino) phosphoranylideneamino]phosphonium chloride, which comprises:

adding an aqueous solution of hydrogen chloride to a feed solution, which contains at least the tetrakis[tris(dimethylamino)phosphoranylideneamino]phosphonium chloride and a substantially water-immiscible organic solvent, either after washing the feed solution with water or without washing the same, whereby the tetrakis[tris(dimethylamino)phosphoranylideneamino]phosphonium chloride is extracted out in a water phase as [tris(dimethylamino)phosphonioamino]tris[tris(dimethylamino)phosphoranylideneamino]phosphonium dichloride which is a hydrogen chloride addition compound of the chloride; and then neutralizing with the hydroxide of an alkali metal or alkaline earth metal the resulting aqueous solution of the [tris(dimethylamino)phosphonioamino]tris[tris(dimethylamino)phosphoranylideneamino]phosphonium dichloride either as is or after concentration, whereby the tetrakis[tris(dimethylamino)phosphoranylideneamino]phosphonium chloride is regenerated and precipitated as a solid from the aqueous solution of the dichloride.

DETAILED DESCRIPTION OF THE INVENTION AND PREFERRED EMBODIMENTS

Figure 1:
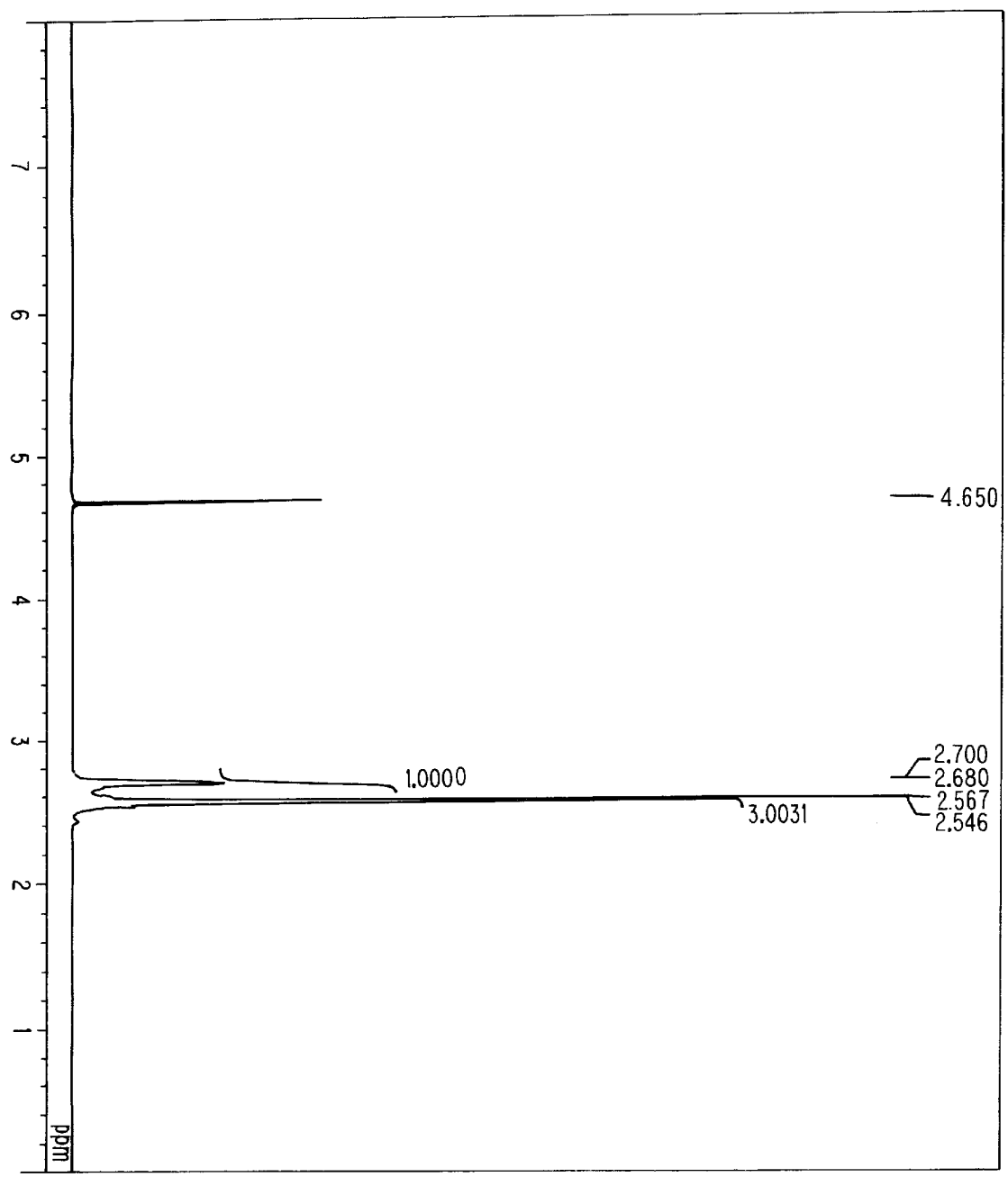
FIG. 1 is a diagram showing a $^1$H-NMR (solvent: $D_2O$) spectrum of a white solid obtained in Example 1, namely [tris(dimethylamino)phosphonioamino]tris[tris(dimethylamino)phosphoranylideneamino]phosphonium dichloride.

[Tris(dimethylamino)phosphonioamino]tris[tris(dimethylamino)phosphoranylideneamino]phosphonium dichloride according to the present invention, which is represented by the formula (1), is a novel compound. This compound can be prepared by bringing hydrogen chloride into contact with tetrakis[tris(dimethylamino)phosphoranylideneamino]phosphonium chloride and adding the former on the latter.

No particular limitation is imposed on its preparation process. Any process may be employed, insofar as it assures effective contact of hydrogen chloride with tetrakis[tris(dimethylamino)phosphoranylideneamino]phosphonium chloride and the object is not inconvenienced. Usable examples of hydrogen chloride can include gaseous hydrogen chloride; compounds capable of releasing hydrogen chloride in their molecules upon heating or the like in the reaction system, for example, tert-butyl chloride; an aqueous solution of hydrogen chloride; and solutions of hydrogen chloride in organic solvents. Among these, an aqueous solution of hydrogen chloride is preferred.

As a method for effectively bringing hydrogen chloride into contact with tetrakis[tris(dimethylamino)phosphoranylideneamino]phosphonium chloride, they are usually brought into contact in a liquid phase. It is particularly preferred to bring tetrakis[tris(dimethylamino)phosphoranylideneamino]phosphonium chloride and hydrogen chloride into mutual contact by a method making use of a uniform system, namely forming tetrakis[tris(dimethylamino)phosphoranylideneamino]phosphonium chloride into an aqueous solution and then adding an aqueous solution of hydrogen chloride to the aqueous solution of the chloride or by a method relying upon a two-phase system, namely by forming the chloride into a solution of a substantially water-immiscible organic solvent and then adding an aqueous solution of hydrogen chloride to the solution of the chloride.

According to the former method, a solution of [tris(dimethylamino)phosphonioamino]tris[tris(dimethylamino)phosphoranylideneamino]phosphonium dichloride is directly obtained. According to the latter method, on the other hand, an aqueous solution of [tris(dimethylamino)phosphonioamino]tris[tris(dimethylamino)phosphoranylideneamino]phosphonium dichloride is obtained by efficiently stirring the two phases, permitting the resultant mixture to stand still to allow it to separate into a water phase and an organic phase, and then collecting the water phase.

Among these methods, more preferred is the method in which tetrakis[tris(dimethylamino)phosphoranylideneamino]phosphonium chloride is formed into a solution in the substantially water-immiscible organic solvent and hydrogen chloride is brought into contact as an aqueous solution of hydrogen chloride.

No particular limitation is imposed on the amount of hydrogen chloride upon bringing tetrakis[tris(dimethylamino)phosphoranylideneamino]phosphonium chloride and hydrogen chloride into mutual contact in the process of the present invention, but hydrogen chloride may be brought into contact in an amount of from 0.5 to 2 mol, preferably from 0.9 to 1.2 mol per mol of tetrakis[tris(dimethylamino)phosphoranylideneamino]phosphonium chloride.

No particular limitation is imposed on the temperature and time upon contacting them together, but the temperature may be from 10 to 80° C., preferably from 15 to 35° C. and the time may be not longer than 3 hours, preferably from 0.01 to 1 hour, preferably from 0.05 to 0.5 hour.

When a solvent is used, no particular limitation is imposed on the amount of the solvent. The amount of the solvent may be generally 500 parts by weight or less, preferably from 0.1 to 50 parts by weight per part by weight of tetrakis[tris(dimethylamino)phosphoranylideneamino]phosphonium chloride.

As will be demonstrated in Examples 1–4, it is evident that the contact of hydrogen chloride with tetrakis[tris(dimethylamino)phosphoranylideneamino]phosphonium chloride forms the hydrogen chloride addition compound of the chloride, namely, [tris(dimethylamino)phosphonioamino]tris[tris(dimethylamino)phosphoranylideneamino]phosphonium dichloride represented by the formula (1).

Although this compound is represented by the formula (1) in the present invention, this formula is only one of possible canonical structural formulas and it may take another canonical structural formula. As a matter of fact, this compound is a resonance hybrid of such canonical structural formulas. Further, the bonds between two phosphorus atoms and two chlorine atoms in the formula (1) are shown in the form of ionic bonds. As equally applied to many compounds having ionic bonding property, the formula (1) should not be interpreted as negating the possibility that the bonds between these phosphorus atoms and chlorine atoms actually have some covalent bonding property. [Tris (dimethylamino)phosphonioamino]tris[tris(dimethylamino) phosphoranylideneamino]phosphonium dichloride according to the present invention embraces all of such structural alternatives.

[Tris(dimethylamino)phosphonioamino]tris[tris (dimethylamino)phosphoranylideneamino]phosphonium dichloride is generally obtained in the form of an aqueous solution as described above. If necessary, this compound can be collected as a solid by a method commonly employed in the art, for example, by concentrating the aqueous solution to dryness or by cooling the aqueous solution, as is or after concentration, to allow the compound to crystallize out as a precipitate.

The term "substantially water-immiscible organic solvent" as used herein means an organic solvent, which is used in ordinary extraction or the like, is not soluble in water to such an extent as posing a problem and is readily separable from a water phase. In addition, it is not supposed to undergo any chemical change even when brought into contact with tetrakis[tris(dimethylamino)phosphoranylideneamino] phosphonium chloride and the aqueous solution of hydrogen chloride.

Illustrative of such a substantially water-immiscible organic solvent are:
saturated aliphatic hydrocarbons such as pentane, hexane, cyclohexane, heptane, octane, nonane, and decane;
benzene;
alkyl-substituted aromatic hydrocarbons such as toluene, o-xylene, m-xylene, p-xylene, ethylbenzene, n-propylbenzene, cumene, 1,2,3-trimethylbenzene, 1,2, 4-trimethylbenzene, mesitylene, tetralin, butylbenzene, p-cymene, cyclohexylbenzene, 1,2-diethylbenzene, 1,3-diethylbenzene, 1,4-diethylbenzene, 1,2-diisopropylbenzene, 1,3-diisopropylbenzene, 1,4-diisopropylbenzene, 1,2,4-triethylbenzene, 1,3,5-triethylbenzene, and dodecylbenzene;
halogenated aromatic hydrocarbons such as chlorobenzene, o-dichlorobenzene, m-dichlorobenzene, 1,2,4-trichlorobenzene, bromobenzene, o-dibromobenzene, m-dibromobenzene, 1-bromo-2-chlorobenzene, 1-bromo-3-chlorobenzene, 1-chloronaphthalene, and 1-bromonaphthalene;
halogenated and alkyl-substituted aromatic hydrocarbons such as 2-chlorotoluene, 3-chlorotoluene, 4-chlorotoluene, 2-bromotoluene, 3-bromotoluene, 2,4-dichlorotoluene, 3,4-dichlorotoluene, 1-chloro-2-ethylbenzene, 1-chloro-4-ethylbenzene, 1-bromo-2-ethylbenzene, 1-bromo-4-ethylbenzene, 1-chloro-4-isopropylbenzene, 1-bromo-4-isopropylbenzene, mesityl chloride, 2-chloro-o-xylene, and 4-chloro-o-xylene;
ethers such as diethyl ether, diisopropyl ether, dibutyl ether, 1,4-dioxane, ethylene glycol dimethyl ether, diethylene glycol dimethyl ether, anisole, o-dimethoxybenzene, ethyl phenyl ether, butyl phenyl ether, and o-diethoxy benzene; and
chlorinated aliphatic hydrocarbons such as carbon tetrachloride, chloroform, dichloromethane, 1,1,2-trichloroethylene, and tetrachloroethylene.

Other solvents may also be used insofar as they do not impair the process according to the present invention.

Among these, preferred examples can include:
saturated aliphatic hydrocarbons having 6–8 carbon atoms, such as hexane, cyclohexane, heptane, and octane;
benzene;
alkyl-substituted aromatic hydrocarbons having 7–9 carbon atoms, such as toluene, o-xylene, m-xylene, p-xylene, ethylbenzene, and mesitylene;
chlorinated benzenes having 1–3 chlorine atoms, such as chlorobenzene, o-dichlorobenzene, m-dichlorobenzene, and 1,2,4-trichlorobenzene;
chlorinated and alkyl-substituted aromatic hydrocarbons having 7–9 carbon atoms and 1–2 chlorine atoms, such as 2-chlorotoluene, 2,4-dichlorotoluene, 1-chloro-4-ethylbenzene, and mesityl chloride; and
ethers having 4–8 carbon atoms, such as diethyl ether, 1,4-dioxane, ethylene glycol dimethyl ether, diethylene glycol dimethyl ether, anisole, o-dimethoxybenzene, and ethyl phenyl ether.

These substantially water-immiscible organic solvents may be used either singly or in combination. No particular limitation is imposed on the amount of such an organic solvent, but per part by weight of tetrakis[tris (dimethylamino)phosphoranylideneamino]phosphonium chloride contained in a solution containing at least the chloride and the substantially water-immiscible organic solvent, the amount of the organic solvent may be not greater than 500 parts by weight, preferably 1 to 100 parts by weight, more preferably 1.5 to 20 parts by weight.

The term "the solution containing at least tetrakis[tris (dimethylamino)phosphoranylideneamino]phosphonium chloride and the substantially water-immiscible organic solvent" in the process of the present invention means a solution containing at least the two components. It may also contain other components insofar as they do no impair the process of the present invention.

Further, this solution may be a solution formed by dissolving once-separated tetrakis[tris(dimethylamino) phosphoranylideneamino]phosphonium chloride in the organic solvent. In this case, a portion of the chloride may be contained in its undissolved form.

In addition, the solution containing at least tetrakis[tris (dimethylamino)phosphoranylideneamino]phosphonium chloride and the substantially water-immiscible organic solvent may be a solution available by removing solid aminotris(dimethylamino)phosphonium chloride by solid-liquid separation from a reaction mixture obtained by reacting phosphorus pentachloride with iminotris (dimethylamino)phosphorane and containing tetrakis[tris (dimethylamino)phosphoranylideneamino]phosphonium chloride, said solid aminotris(dimethylamino)phosphonium chloride being a by-product in the reaction. If necessary, it may also be a solution obtained by removing the solvent of the thus-obtained solution by a method such as distillation and then adding a desired, substantially water-immiscible organic solvent as a substitute.

Of these solutions, use of the solution—which is available by removing solid aminotris(dimethylamino)phosphonium chloride by solid-liquid separation from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a by-product in the reaction— is important from the viewpoint that tetrakis[tris (dimethylamino)phosphoranylideneamino]phosphonium chloride be separated from an organic phase.

Preferred as such a solution is a solution available by removing solid aminotris(dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino)phosphoranylideneamino]phosphonium chloride, said solid aminotris(dimethylamino)phosphonium chloride being a by-product in said reaction.

Incidentally, the term "initial stage" as used herein means an initial stage of the reaction, including a preparatory time during which phosphorus pentachloride and iminotris(dimethylamino)phosphorane are brought into contact with each other.

In the process of the present invention, the solution which contains at least tetrakis[tris(dimethylamino)phosphoranylideneamino]phosphonium chloride and the substantially water-immiscible organic solvent may be washed with water before its treatment with the aqueous solution of hydrogen chloride.

As a method for conducting this water washing, any method can be used insofar as it can assure sufficient contact between the solution and water. After washing, the solution can be recovered by permitting the resulting mixture to stand still to allow it to separate into an organic phase and a water phase and then removing the water phase.

Although no particular limitation is imposed on the amount of water in this water washing, water can be used generally in an amount of 5 parts by weight or less per weight of the solution containing at least tetrakis[tris(dimethylamino)phosphoranylideneamino]phosphonium chloride and the substantially water-immiscible organic solvent.

The solution may be washed several times with such an amount of water. Preferably, the solution may be washed 2 to 5 times with water in an amount of from 0.05 to 1.0 part by weight per part by weight of the solution each time. No particular limitation is imposed on the washing temperature or time, but the temperature may range generally from 10 to 80° C., preferably from 15 to 35° C., and the time may be 3 hours or less in general, preferably 0.01 to 1 hour, more preferably 0.05 to 0.5 hour.

It is an object of this water washing to eliminate water-soluble substances contained in the solution which contains at least tetrakis[tris(dimethylamino)phosphoranylideneamino]phosphonium chloride and the substantially water-immiscible organic solvent.

Especially in the solution available by removing solid aminotris(dimethylamino)phosphonium chloride by solid-liquid separation from a reaction mixture obtained by reacting phosphorus pentachloride with iminotris(dimethylamino)phosphorane and containing tetrakis[tris(dimethylamino)phosphoranylideneamino]phosphonium chloride, said solid aminotris(dimethylamino)phosphonium chloride being a by-product in the reaction, small amounts of the raw materials and by-products—such as the unreacted iminotris(dimethylamino)phosphorane and aminotris(dimethylamino)phosphonium chloride still remaining in a dissolved form despite the solid-liquid separation—and trace amounts of impurities are present. They can be washed out almost completely into a water phase by this water washing.

On the other hand, tetrakis[tris(dimethylamino)phosphoranylideneamino]phosphonium chloride is practically unpartitioned into the water phase because it is dissolved extremely well in the organic solvent.

When the partition ratios by weight of iminotris(dimethylamino)phosphorane, aminotris(dimethylamino)phosphonium chloride and tetrakis[tris(dimethylamino)phosphoranylideneamino]phosphonium chloride into a water phase and an organic phase consisting of o-dichlorobenzene were measured by setting the weight ratio of water to o-dichlorobenzene solvent, for example, at 1:4, they were found to be 89.5/10.5 (water phase/organic phase, this will apply equally hereinafter), 99.5/0.5 and $\leqq 0.1/\geqq 99.9$, respectively.

As is appreciated from the foregoing, this water washing is very effective for the elimination of small amounts of water-soluble raw materials and by-products.

On the other hand, the above-mentioned water washing can be omitted when the solution containing at least tetrakis[tris(dimethylamino)phosphoranylideneamino]phosphonium chloride and the substantially water-immiscible organic solvent is a solution from which water-soluble raw materials, by-products and impurities contained therein have been eliminated beforehand by a certain method or when the treatment is applied to a solution free of water-soluble substances such as a solution formed by dissolving once-separated tetrakis[tris(dimethylamino)phosphoranylideneamino]phosphonium chloride in a substantially water-immiscible solvent.

When the solution containing at least tetrakis[tris(dimethylamino)phosphoranylideneamino]phosphonium chloride and the substantially water-immiscible organic solvent is added, either after being washed with water or without being washed with water, with an aqueous solution of hydrogen chloride and both the solutions are efficiently brought into contact, the hydrogen chloride and the tetrakis[tris(dimethylamino)phosphoranylideneamino]phosphonium chloride are promptly formed into the hydrogen chloride addition compound of the chloride, namely, [tris(dimethylamino)phosphonioamino]tris[tris(dimethylamino)phosphoranylideneamino]phosphonium dichloride.

The water solubility of this compound is considerably higher than that of its starting material, i.e., tetrakis[tris(dimethylamino)phosphoranylideneamino]phosphonium chloride, whereas its solubility in the organic solvent is lower than that of the starting material.

Owing to this feature, tetrakis[tris(dimethylamino)phosphoranylideneamino]phosphonium chloride can be transferred as [tris(dimethylamino)phosphonioamino]tris[tris(dimethylamino)phosphoranylideneamino]phosphonium dichloride into a water phase with extremely high efficiency, thereby permitting its extraction and separation. After the resulting mixture is permitted to stand still, the water phase and the organic phase are separated from each other so that [tris(dimethylamino)phosphonioamino]tris[tris(dimethylamino)phosphoranylideneamino]phosphonium dichloride can be collected as an aqueous solution.

Upon extracting with the aqueous solution of hydrogen chloride tetrakis[tris(dimethylamino)phosphoranylideneamino]phosphonium chloride—which is contained in the substantially water-immiscible organic solvent—as [tris(dimethylamino)phosphonioamino]tris[tris(dimethylamino)phosphoranylideneamino]phosphonium dichloride into the water phase and obtaining the aqueous solution of the dichloride, no particular limitation is imposed on the amount of the hydrogen chloride in its aqueous solution. In general, however, the amount of hydrogen chloride may range from 0.5 to 2 mol, preferably from 0.9 to 1.2 mol per mol of tetrakis[tris(dimethylamino)phosphoranylideneamino]phosphonium chloride.

Where the solution containing at least tetrakis[tris(dimethylamino)phosphoranylideneamino]phosphonium chloride and the substantially water-immiscible organic solvent contains a portion of the chloride in an undissolved form, the above-mentioned amount is the amount per mole of the sum of the dissolved portion and undissolved portion of the chloride.

Hydrogen chloride in such an amount is used as an aqueous solution. The amount of water used here is generally 100 parts by weight or less, preferably 10 parts by weight or less, more preferably 5 parts by weight or less per part of the solution containing at least tetrakis[tris(dimethylamino)phosphoranylideneamino]phosphonium chloride and the substantially water-immiscible organic solvent.

No particular limitation is imposed on the temperature or time upon bringing the aqueous solution of hydrogen chloride into contact with the solution. However, the temperature may range generally from 10 to 80° C., preferably from 15 to 35° C., while the time may be 3 hours or less in general, preferably 0.01 to 1 hour, more preferably 0.05 to 0.5 hour.

As has been described above, the tetrakis[tris(dimethylamino)phosphoranylideneamino]phosphonium chloride in the solution, which contains at least tetrakis[tris(dimethylamino)phosphoranylideneamino]phosphonium chloride and the substantially water-immiscible organic solvent, can be extracted and separated as the hydrogen chloride addition compound of the chloride, i.e., [tris(dimethylamino)phosphonioamino]tris[tris(dimethylamino)phosphoranylideneamino]phosphonium dichloride in a water phase by bringing the solution, either after washing it with water or without washing it with water, into contact with the thus-added aqueous solution of hydrogen chloride, thereby making it possible to separate the tetrakis[tris(dimethylamino)phosphoranylideneamino]phosphonium chloride.

Further, the aqueous solution of [tris(dimethylamino)phosphonioamino]tris [tris(dimethylamino)phosphoranylideneamino]phosphonium dichloride—which is obtained by bringing the aqueous solution of hydrogen chloride into contact with the solution containing at least tetrakis[tris(dimethylamino)phosphoranylideneamino]phosphonium chloride and the substantially water-immiscible organic solvent, either after washing it with water or without washing it with water, and extracting and separating the tetrakis[tris(dimethylamino)phosphoranylideneamino]phosphonium chloride as the hydrogen chloride addition compound of the chloride, namely, [tris(dimethylamino)phosphonioamino]tris[tris(dimethylamino)phosphoranylideneamino]phosphonium dichloride in the water phase—may be provided, as is, for the subsequent use. As an alternative, the [tris(dimethylamino)phosphonioamino]tris[tris(dimethylamino)phosphoranylideneamino]phosphonium dichloride may be isolated by a method commonly employed in the art, for example, by concentrating the aqueous solution to dryness or by concentrating and/or cooling the aqueous solution so that the dichloride is allowed to crystallize out as a precipitate.

According to the process of the present invention, tetrakis [tris(dimethylamino)phosphoranylideneamino] phosphonium hydroxide can be prepared by bringing the solution containing at least tetrakis[tris(dimethylamino)phosphoranylideneamino]phosphonium chloride and the substantially water-immiscible organic solvent, either after washing it with water or without washing it with water, into contact with an added aqueous solution of hydrogen chloride to extract the tetrakis[tris(dimethylamino)phosphoranylideneamino]phosphonium chloride as the hydrogen chloride addition compound of the chloride, namely, [tris(dimethylamino)phosphonioamino]tris[tris(dimethylamino)phosphoranylideneamino]phosphonium dichloride in a water phase and then bringing the resulting solution of [tris(dimethylamino)phosphonioamino]tris[tris(dimethylamino)phosphoranylideneamino]phosphonium dichloride into contact with an OH⁻-form ion exchange resin.

Although no particular limitation is imposed on the method for this contact, ion exchange is usually conducted by packing the resin in a column and causing the aqueous solution of the dichloride to flow through the thus-packed column. The OH⁻-form ion exchange resin employed here is usually one of the tertiary amine or quaternary ammonium type.

In the above contact, the resin is used in such an amount that the ion exchange capacity of the resin may range generally from 1 to 100 molar times, preferably from 1.5 to 20 molar times relative to the sum of the twofold value of the number of moles of the [tris(dimethylamino)phosphonioamino]tris[tris(dimethylamino)phosphoranylideneamino]phosphonium dichloride in the aqueous solution to be subjected to ion exchange and the number of moles of hydrogen chloride, if still remaining.

An aqueous solution of tetrakis[tris(dimethylamino)phosphoranylideneamino]phosphonium hydroxide can be obtained conveniently and efficiently from [tris(dimethylamino)phosphonioamino]tris[tris(dimethylamino)phosphoranylideneamino]phosphonium dichloride as described above.

Usually, this aqueous solution is an aqueous solution of tetrakis[tris(dimethylamino)phosphoranylideneamino] phosphonium hydroxide having sufficiently high purity.

Further, from the thus-obtained aqueous solution of tetrakis[tris(dimethylamino)phosphoranylideneamino] phosphonium hydroxide, the hydroxide can be collected as a solid by distilling off water.

Upon distilling off water from the aqueous solution, the distillation is conducted usually at 100° C. or lower. It is preferred to conduct the distillation at 80° C. or lower under reduced pressure. The solid may also be subjected to purification such as reprecipitation, if necessary.

According to the process of the present invention, the aqueous solution of [tris(dimethylamino)phosphonioamino] tris[tris(dimethylamino)phosphoranylideneamino] phosphonium dichloride—which is obtained by bringing the solution containing at least tetrakis[tris(dimethylamino)phosphoranylideneamino]phosphonium chloride and the substantially water-immiscible organic solvent, either after washing it with water or without washing it with water, into contact with the added aqueous solution of hydrogen chloride to extract the tetrakis[tris(dimethylamino)phosphoranylideneamino]phosphonium chloride as the hydrogen chloride addition compound of the chloride, namely, [tris(dimethylamino)phosphonioamino]tris[tris(dimethylamino)phosphoranylideneamino]phosphonium dichloride—is neutralized, either as is or after concentration, with an alkali metal hydroxide or alkaline earth metal hydroxide to regenerate tetrakis[tris(dimethylamino)phosphoranylideneamino]phosphonium chloride, and the tetrakis[tris(dimethylamino)phosphoranylideneamino]phosphonium chloride is then isolated by allowing it to precipitate as a solid from the aqueous solution.

Among alkali metal hydroxides and alkaline earth metal hydroxides, alkali metal hydroxides are preferred, with sodium hydroxide and potassium hydroxide being more preferred.

The number of equivalents of the alkali metal hydroxide or alkaline earth metal hydroxide employed for the neutralization may range generally from 0.7 to 1.5 times, preferably from 0.8 to 1.2 times relative to the sum of the number of moles of the [tris(dimethylamino)phosphonioamino]tris[tris(dimethylamino)phosphoranylideneamino]phosphonium dichloride in the aqueous solution of the dichloride, in other words, the number of moles of the hydrogen chloride incorporated upon formation of the dichloride and the number of moles of hydrogen chloride which may exist in the aqueous solution in some instances.

The concentration of the aqueous solution to be neutralized may range generally from 5 to 50 wt. %, preferably from 10 to 40 wt. %. Upon concentration, the neutralization salt of the alkali metal hydroxide or alkaline earth metal hydroxide and hydrogen chloride is formed. This salt usually occurs in an amount small enough to be dissolved fully in the water. On the other hand, the solubility of tetrakis[tris(dimethylamino)phosphoranylideneamino]phosphonium chloride in water is sufficiently low so that the chloride precipitates with priority. The chloride can therefore be easily separated by a conventional solid-liquid separation method, for example, filtration or the like. The neutralization is usually conducted at room temperature.

According to the process of the present invention, the thus-regenerated tetrakis[tris(dimethylamino)phosphoranylideneamino]phosphonium chloride is seldom converted further into tetrakis[tris(dimethylamino)phosphoranylideneamino]phosphonium hydroxide even when the alkali metal hydroxide or alkaline earth metal hydroxide is used in excess upon neutralization.

The tetrakis[tris(dimethylamino)phosphoranylideneamino]phosphonium chloride, which has been obtained by conducting regeneration and precipitation as described above, has sufficiently high purity. Nonetheless, it may be purified further by recrystallization if necessary.

The present invention will next be described in further detail by examples, which should be interpreted merely as illustrative rather than as limiting.

EXAMPLE 1

Synthesis of [Tris(dimethylamino)phosphonioamino]tris[tris(dimethylamino)phosphoranylideneamino]phosphonium Dichloride Into a 300-ml eggplant flask equipped with a thermometer, a dropping funnel and a stirrer, 3.01 g (3.88 mmol) of tetrakis[tris(dimethylamino)phosphoranylideneamino]phosphonium chloride and 101 g of water were added to form a solution. The concentration was 2.89 wt. %. While stirring the solution, 3.88 ml of a 1 N aqueous solution of hydrogen chloride (factor: 1.000) (hydrogen chloride: 3.88 mmol) were gradually added little by little from the dropping funnel. Subsequent to stirring at room temperature for 0.2 hour, the aqueous solution was concentrated to dryness, whereby 3.15 g of a white solid were obtained.

This white solid (108.9 mg) was dissolved in 20 ml of water, and the resulting solution was subjected to a quantitative analysis of chloride ions by the Mohr method making use of a 2 wt. % aqueous solution of potassium chromate and an aqueous solution of silver nitrate. As a result, the white solid was found to contain chlorine at a concentration of 8.77 wt. %, which was in good conformity with 8.73 wt. % as the chlorine content in [tris(dimethylamino)phosphonioamino]tris[tris(dimethylamino)phosphoranylideneamino]phosphonium dichloride, the 1:1 addition compound of tetrakis[tris(dimethylamino)phosphoranylideneamino]phosphonium chloride and hydrogen chloride.

Elemental analysis (wt. %):
Found: C: 35.70, H: 8.99, N: 27.61, P: 18.95, Cl: 8.75 (Calculated: C: 35.51, H: 9.06, N: 27.61, P: 19.08, Cl: 8.73).

Figure 2:
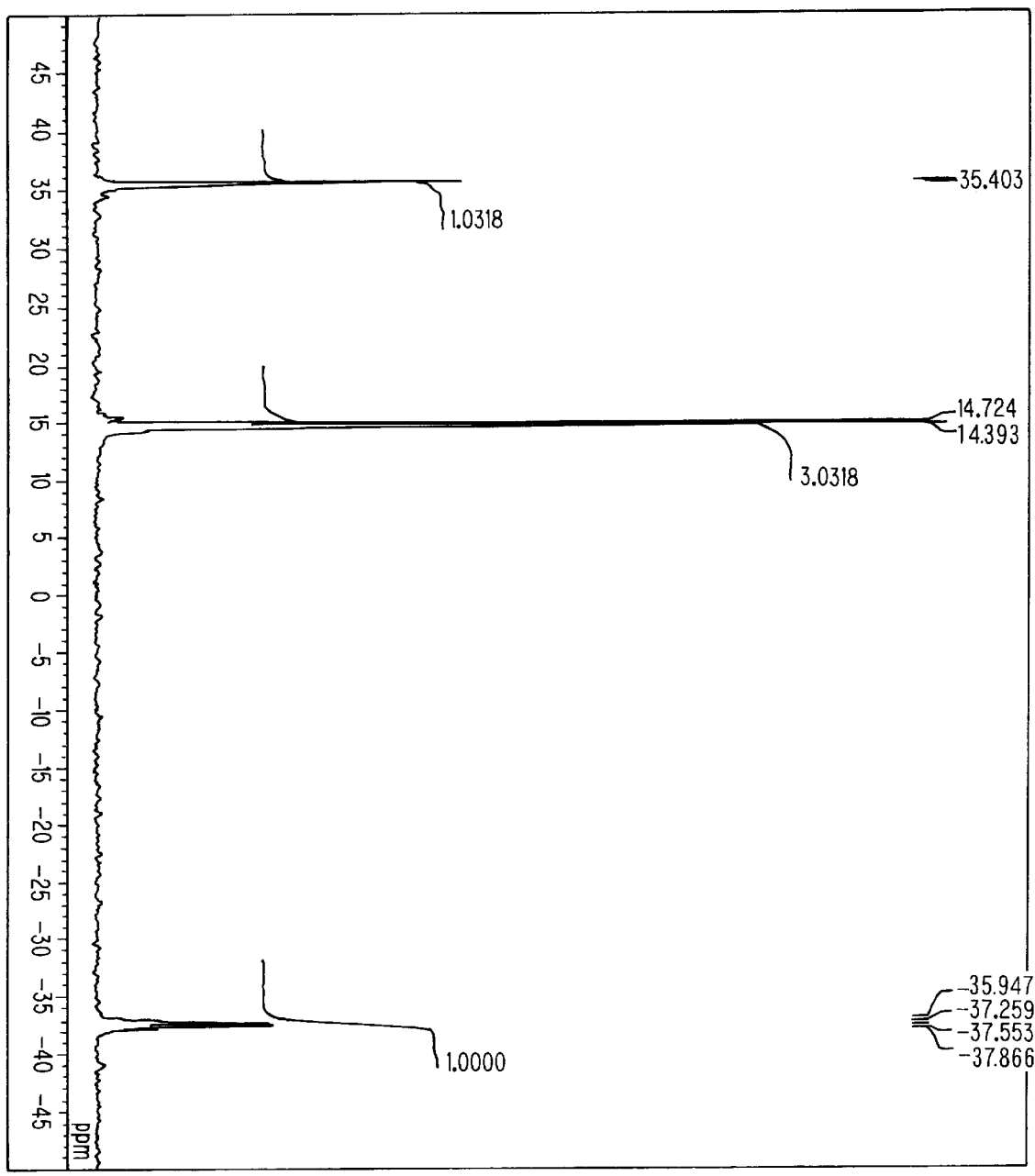
FIG. 2 is a diagram showing a $^{31}$P-NMR (solvent: $D_2O$) spectrum of the white solid obtained in Example 1, namely [tris(dimethylamino)phosphonioamino]tris[tris(dimethylamino)phosphoranylideneamino]phosphonium dichloride.

$^1$H-NMR and $^{31}$P-NMR spectra of a solution of the white solid, which had been obtained from the water phase, in heavy water ($D_2O$) were measured. The results are shown in FIG. 1 and FIG. 2. When a signal of HDO formed as a result of an H-D interchange in the system was brought into registration with 4.65 ppm, the $^1$H-NMR spectrum (FIG. 1) of this compound were observed to contain chemical shifts at 2.69 and 2.56 ppm.

These chemical shifts can be ascribed to two methyl groups which are in different environments, and are observed as doublets because of their coupling to phosphorus atoms. The difference in the chemical shifts due to the difference in environment between these methyl groups can be attributed to the formation of NH—P$^+$ by the addition of the hydrogen atom of hydrogen chloride to only one of the N=P double bonds of the four tris(dimethylamino)phosphoranylideneamino groups in the starting compound, i.e., tetrakis[tris(dimethylamino)phosphoranylideneamino]phosphonium chloride. As a result, their integrals are at a ratio of 3.0081:1.000, namely 3:1 as is indicated in FIG. 1.

On the other hand, chemical shifts appeared at 35.4, 14.6 and −37.4 ppm in the $^{31}$P-NMR spectrum (FIG. 2) when observed with a signal of the phosphorus atom of 85% phosphoric acid brought into registration with 0 ppm by an external standard method. These chemical shifts were derived from the three types of phosphorus atoms in the formula (1) and successively from the side of a low magnetic field, can be ascribed to the phosphorus atom in only one of the N=P double bonds of the four tris(dimethylamino)phosphoranylideneamino groups in the starting compound, i.e., tetrakis[tris(dimethylamino)phosphoranylideneamino]phosphonium chloride, said phosphorus atom being in the form of a cation as a result of the formation of NH—P$^+$ by the addition of the hydrogen atom of the hydrogen chloride, the remaining three phosphorus atoms of N=P double bonds, and the central phosphorus atom, respectively. As a result, their integrals are at a ratio of 1.0318:3.0318:1.0000, namely 1:3:1 as is indicated in FIG. 2.

Assuming that the white solid was [tris(dimethylamino)phosphonioamino]tris[tris(dimethylamino)phosphoranylideneamino]phosphonium dichloride, three acetonitrile solutions of different concentrations were prepared. Their concentrations were 10.0, 1.00 and 0.100 mM.

The electrical conductivities of these solutions were measured. They were found to be 2620, 323 and 31.7 μS, respectively. On the other hand, three acetonitrile solutions of sodium iodide were prepared, the concentrations of which were the same as above. The electrical conductivities of these three solutions were measured in the same manner. As a result, they were found to be 1250, 143 and 15.1 μS, respectively.

According to a comparison in the value of electrical conductivity between [tris(dimethylamino)phosphonioamino]tris[tris(dimethylamino)phosphoranylideneamino]phosphonium dichloride and sodium iodide at the respective concentrations, the former was found to have a value about twice as high as the latter. This indicates that [tris(dimethylamino)phosphonioamino]tris[tris(dimethylamino)phosphoranylideneamino]

phosphonium dichloride exists as divalent ions in the acetonitrile solution.

From the information on all of these analyses, it is evident that the white solid obtained as described above is the 1:1 addition compound of tetrakis[tris(dimethylamino) phosphoranylideneamino]phosphonium chloride and hydrogen chloride, namely [tris(dimethylamino) phosphonioamino]tris[tris(dimethylamino) phosphoranylideneamino]phosphonium dichloride the structure of which is represented by the formula (1).

EXAMPLE 2

In a 500-ml separating funnel, 15.5 g (20.0 mmol) of tetrakis[tris(dimethylamino)phosphoranylideneamino] phosphonium chloride were weighed, followed by the addition of 63.4 g of o-dichlorobenzene so that the former was completely dissolved in the latter. 1 N hydrochloric acid (factor: 1.000) was added in an amount of precisely 20.0 ml (hydrogen chloride: 20.0 mmol) to 43.0 g of water, whereby an aqueous solution of hydrogen chloride was prepared. This aqueous solution of hydrogen chloride was gradually added little by little to the o-dichlorobenzene solution of the chloride.

After the addition of the aqueous solution in its entirety, the separating funnel was strongly shaken at room temperature for 0.1 hour to bring both of the phases into contact with each other and the resulting mixture was then permitted to stand still. Subsequent to full separation into an organic phase and a water phase, both of the phases were collected separately. The amount of the organic phase was 63.8 g, while that of the water phase was 78.0 g. When the whole organic phase and a portion (25.0 g) of the water phase were concentrated to dryness, respectively, the organic phase gave substantially no residue whereas the water phase gave a white solid in an amount as much as 5.18 g.

From a similar chlorine analysis as in Example 1, the solid was determined to contain chlorine at a concentration of 8.75 wt. % (theoretical value: 8.73 wt. %), and its $^{31}$P-NMR spectrum as measured in heavy water was exactly the same as that shown in FIG. 2.

EXAMPLE 3

Into a 300-ml eggplant flask equipped with a thermometer, a stirrer and a gas inlet tube, 31.2 g (40.2 mmol) of tetrakis[tris(dimethylamino) phosphoranylideneamino]phosphonium chloride and 103 g of toluene were added to form a solution. The reaction system was sealed with nitrogen, and under stirring at room temperature, gaseous hydrogen chloride was charged from a cylinder while maintaining the tip of the inlet tube at a level slightly higher than the liquid level. From shortly after that, the solution began to become turbid, and the turbidity of the solution increased with time. After hydrogen chloride were charged to an amount of 1.76 g (48.2 mmol), the reaction mixture was stirred further for 0.2 hour.

The resultant white solid was collected by filtration, washed first with a small amount of toluene and then with a small amount of n-hexane, and then fully dried under reduced, pressure, whereby 32.6 g of a solid was obtained.

From a similar chlorine analysis as in Example 1, the solid was determined to contain chlorine at a concentration of 8.76 wt. % (theoretical value: 8.73 wt. %), and its $^{31}$P-NMR spectrum as measured in heavy water was the same as that shown in FIG. 2.

EXAMPLE 4

Into a 200-ml conical beaker, 2.979 g (3.843 mmol) of tetrakis[tris(dimethylamino)phosphoranylideneamino] phosphonium chloride and 98.85 g of water were added to form a solution. The concentration of the solution was 2.924 wt. %.

Figure 3:
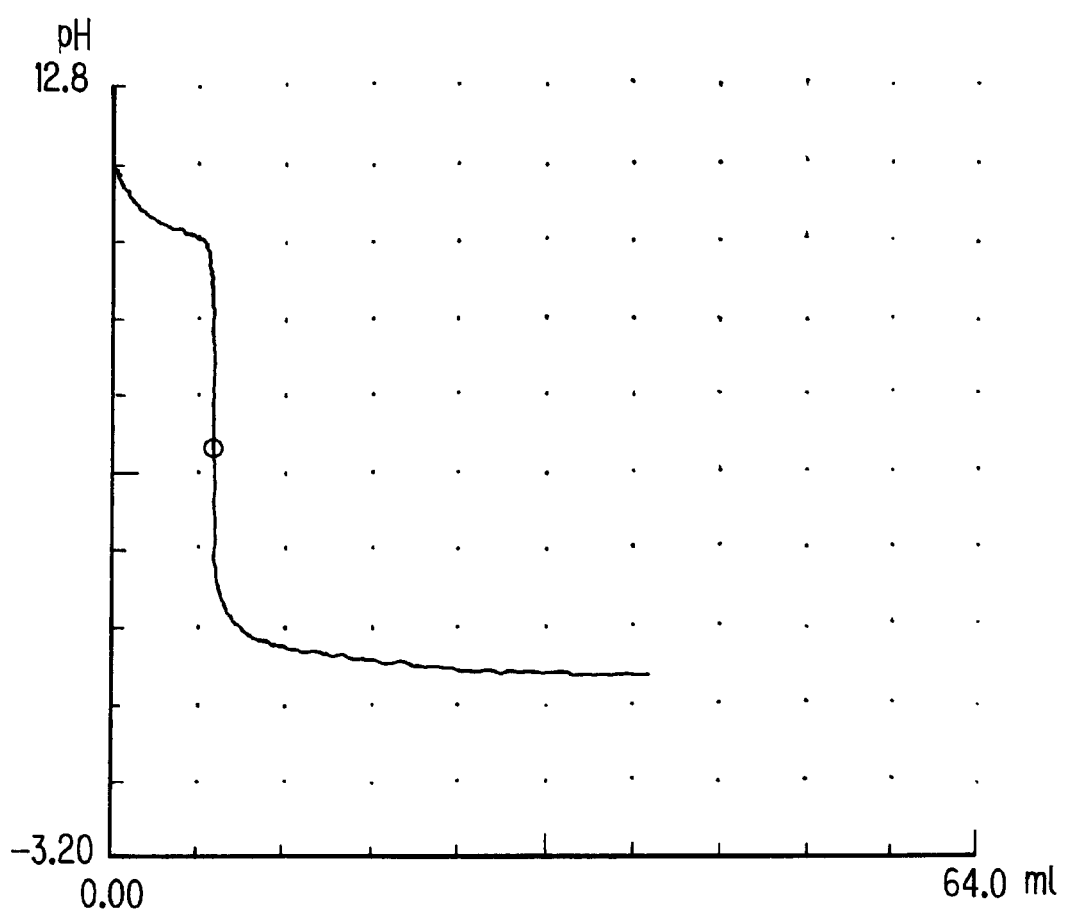
FIG. 3 is a diagram showing a pH curve obtained when an aqueous solution of hydrogen chloride was progressively added to an aqueous solution of tetrakis[tris(dimethylamino)phosphoranylideneamino]phosphonium chloride.

While adding a 0.05 N (factor: 1.006) aqueous solution of hydrogen chloride at room temperature to the solution, the pH of the resulting mixture was monitored by an automatic pH measuring instrument. A pH curve was obtained as shown in FIG. 3. An inflection point occured when hydrogen chloride was added in exactly the equimolar amount as tetrakis[tris(dimethylamino)phosphoranylideneamino] phosphonium chloride, and no other inflection point appeared even when hydrogen chloride was added up to an amount 5 molar times as much as the chloride.

From the foregoing, it has been found that tetrakis[tris (dimethylamino)phosphoranylideneamino]phosphonium chloride and hydrogen chloride forms only the 1:1 addition compound, namely [tris(dimethylamino)phosphonioamino] tris[tris(dimethylamino)phosphoranylideneamino] phosphonium dichloride.

EXAMPLE 5

In a 300-ml separating funnel, 9.30 g (12.0 mmol) of tetrakis[tris(dimethylamino)phosphoranylideneamino] phosphonium chloride were weighed, followed by the addition of 38.0 g of o-dichlorobenzene so that the former was completely dissolved in the latter. 1 N hydrochloric acid (factor: 1.000) was added in an amount of precisely 12.0 ml (hydrogen chloride: 12.0 mmol) to 25.8 g of water, whereby an aqueous solution of hydrogen chloride was prepared. This aqueous solution of hydrogen chloride was gradually added little by little to the o-dichlorobenzene solution of the chloride.

After the addition of the aqueous solution in its entirety, the separating funnel was strongly shaken at room temperature for 0.1 hour to bring both of the phases into contact with each other and the resulting mixture was then permitted to stand still. Subsequent to full separation into an organic phase and a water phase, both of the phases were collected separately. When the whole water phase was concentrated to dryness, a white solid was obtained in an amount as much as 9.55 g. In contrast, substantially no residue was obtained when the organic phase was concentrated to dryness.

When the white solid was analyzed as in Example 1, it was determined to consist of pure [tris(dimethylamino) phosphonioamino]tris[tris(dimethylamino) phosphoranylideneamino]phosphonium dichloride. Its yield was 98.1% based on the tetrakis[tris(dimethylamino) phosphoranylideneamino]phosphonium chloride.

As is readily appreciated from the foregoing, it was possible to separate the tetrakis[tris(dimethylamino) phosphoranylideneamino]phosphonium chloride almost completely from the organic phase into the water phase.

COMPARATIVE EXAMPLE 1

In a similar manner as in Example 5, 9.30 g (12.0 mmol) of tetrakis[tris(dimethylamino)phosphoranylideneamino] phosphonium chloride were weighed in a 300-ml separating funnel, followed by the addition of 38.0 g of o-dichlorobenzene so that the former was completely dissolved in the latter. Water (38.0 g) was then added to the solution.

The resulting mixture was strongly shaken at room temperature for 0.1 hour in a separating funnel to bring both of the phases into contact with each other and the resulting mixture was then premitted to stand still. Subsequent to full separation into an organic phase and a water phase, both of the phases were collected separately. The amount of the organic phase was 47.0 g, while that of the water phase was 38.3 g. When the whole organic phase and the whole water phase were concentrated to dryness, respectively, the organic phase gave a white solid in an amount as much as 9.26 g whereas the water phase gave substantially no residue.

EXAMPLES 6–11

Experiments were conducted in exactly the same manner as in Example 5 except for the use of the solvents in their corresponding amounts as shown in Table 1. In each of Examples 6–11, substantially no residue was obtained when an organic phase was concentrated to dryness. In Table 1, the results are shown together with the results of Example 5.

In Table 1, each yield is the yield of the [tris (dimethylamino)phosphonioamino]tris[tris(dimethylamino) phosphoranylideneamino]phosphonium dichloride as calculated based on the tetrakis[tris(dimethylamino) phosphoranylideneamino]phosphonium chloride used. In Example 10 where cyclohexane was used, a portion of the tetrakis[tris(dimethylamino)phosphoranylideneamino] phosphonium chloride was insoluble at the beginning. A homogeneous water phase was however obtained and the extraction operation was conducted without encountering any problem.

In each of the examples shown in Table 1, it was possible to extract and separate the tetrakis[tris(dimethylamino) phosphoranylideneamino]phosphonium chloride in high yield from the organic phase into the water phase.

EXAMPLE 12

Charged in a glass-made, 2-l reactor were 60.20 g (0.2891 mol) of phosphorus pentachloride and 659.82 g of o-dichlorobenzene which had been dried beforehand to a water content of 10 ppm by molecular sieves 3A. The contents were heated to 40° C. under stirring. While controlling the temperature of the resulting mixture at the same temperature, 439.3 g (2.465 mol) of iminotris (dimethylamino)phosphorane (the molar ratio of the iminotris(dimethylamino)phosphorane to the phosphorus pentachloride: 8.53) were added dropwise to the mixture over 1.0 hour.

Subsequent to the completion of the dropwise addition, the resulting mixture was maintained further at 40° C. for 1.0 hour. The temperature of the mixture was then raised to 170° C. over about 1 hour, at which a reaction was conducted for 9.0 hours.

At this stage, a portion of the reaction mixture was collected and subjected to a mass spectroscopic analysis. A molecular ion peak was observed at 740 which is equivalent to the molecular weight of the cation fragment of tetrakis-[tris(dimethylamino)phosphoranylideneamino] phosphonium chloride. From a quantitative analysis by $^{31}$P-NMR while making use of deuterated dimethyl sulfoxide as a solvent and tri-n-butyl phosphate as an internal standard compound, formation of 0.2840 mol of tetrakis[tris (dimethylamino)phosphoranylideneamino]phosphonium chloride in this reaction was confirmed.

The reaction mixture was a homogeneous liquid when it was hot. When it was allowed to cool down to room temperature, a white solid of aminotris(dimethylamino) phosphonium chloride precipitated in a large amount. This white solid was collected by using a filter press the capacity of which was 1 l, and was then washed with 247.0 g of o-dichlorobenzene. The resulting o-dichlorobenzene solution consisting of the filtrate and the washing was transferred into a 2-l separating funnel, followed by the addition of 173 g of water.

The separating funnel was strongly shaken at room temperature for 0.2 hour, whereby the organic solution and the water were brought into thorough contact. After the resulting mixture was permitted to stand still, the resulting organic phase and water phase were collected separately. The organic phase was again transferred to the separating funnel, and the water washing operation was conducted further twice likewise.

The organic phase washed with water as described above was transferred again to the separating funnel, followed by the addition of 618 g of water and 275 ml of 1 N hydrochloric acid (factor: 1.000) (hydrogen chloride: 0.275 mol). The resultant mixture was thoroughly shaken at room temperature for 0.1 hour, whereby the organic phase and the water phase were brought into thorough contact. After the resulting mixture was permitted to stand still, the resulting organic phase and water phase were collected separately. The amount of the organic phase was 844.7 g, while that of the water phase was 1,132.0 g. When the whole organic phase was concentrated to dryness, 6.5 g of a pale yellow oil was obtained as a residue.

Further, a portion (10.30 g) of the water phase was concentrated to dryness, whereby 1.999 g of a white solid were obtained (this means that 219.7 g of the white solid were contained in the whole water phase). With respect to the white solid obtained from the water phase as described above, an analysis was conducted in a similar manner as in Example 1. As a result, this solid was found to consist of substantially pure [tris(dimethylamino)phosphonioamino] tris[tris(dimethylamino)phosphoranylideneamino] phosphonium dichloride.

Its yield was 93.6% based on the phosphorus pentachloride. Further, its yield was 95.3% based on the tetrakis[tris (dimethylamino)phosphoranylideneamino]phosphonium chloride formed from the reaction between the phosphorus pentachloride and iminotris(dimethylamino)phosphorane.

Even from the use of the solution obtained by removing solid aminotris(dimethyl)phosphonium chloride from the reaction mixture which had in turn been obtained by reaction phosphorus pentachloride and iminotris(dimethylamino) phosphorane and contained tetrakis[tris(dimethylamino) phosphoranylideneamino]phosphonium chloride, said solid aminotris(dimethyl)phosphonium chloride being a by-product in the reaction, it was possible to almost completely separate the chloride as highly pure [tris (dimethylamino)phosphonioamino]tris[tris(dimethylamino) phosphoranylideneamino]phosphonium dichloride from the organic phase into the water phase as described above.

EXAMPLE 13

An o-dichlorobenzene solution consisting of filtrate and the washing was obtained by conducting a reaction and post-treatment in exactly the same manner as in Example 12. When this solution was concentrated to dryness under reduced pressure, 215.7 g of a white solid were obtained. This solid was completely dissolved in 800 g of chlorobenzene, and the resulting solution was transferred into a 2-l separating funnel.

The separating funnel was added with 175 g of water and was then strongly shaken at room temperature for 0.2 hour, whereby the solution and the water were brought into thorough contact to wash the former with the latter. After the resulting mixture was permitted to stand still, the resulting organic phase and water phase were collected separately. The organic phase was again transferred to the separating funnel, and the water washing operation was conducted further twice likewise. The organic phase washed with water as described above was transferred again to the separating funnel, followed by the addition of 600 g of water and 275 ml of 1 N hydrochloric acid (factor: 1.000) (hydrogen chloride: 0.275 mol).

The resultant mixture was thoroughly shaken at room temperature for 0.1 hour, whereby the organic phase and water phase were brought into thorough contact. After the resulting mixture was permitted to standstill, the resulting organic phase and water phase were collected separately. The amount of the organic phase was 811.5 g, while that of the water phase was 1,075.2 g. When the organic phase was completely concentrated to dryness, 7.0 g of a pale yellow oil was obtained as a residue.

Further, a portion (11.50 g) of the water phase was concentrated to dryness, whereby 2.342 g of a white solid were obtained (this means that 219.0 g of the white solid were contained in the water phase).

With respect to the solid obtained from the water phase as described above, an analysis was conducted in a similar manner as in Example 1. As a result, this solid was found to consist of [tris(dimethylamino)phosphonioamino]tris[tris(dimethylamino)phosphoranylideneamino]phosphonium dichloride.

Its yield was 93.3% based on the phosphorus pentachloride. Further, its yield was 95.0% based on the tetrakis[tris(dimethylamino)phosphoranylideneamino]phosphonium chloride formed from the reaction between the phosphorus pentachloride and iminotris(dimethylamino)phosphorane.

EXAMPLE 14

An organic phase and a water phase were separated from each other in exactly the same manner as in Example 12, whereby 1,132.0 g of an aqueous solution containing 214.0 g (0.2636 mol) of [tris(dimethylamino)phosphonioamino]tris[tris(dimethylamino)phosphoranylideneamino]phosphonium dichloride were obtained. Water (6,000 g) was added further to the aqueous solution, and the resulting solution was caused to flow through a column which was packed with 900 ml of an OH⁻-form ion exchange resin of the quaternary ammonium type having ion exchange capacity of 1.1 meq/ml ("Lewatit MP500", product of Bayer AG).

Water (500 g) was then caused to flow through the column, and including the effluent, 7,607 g of an eluate obtained in total. A portion (100.0 g) of the eluate was concentrated to dryness, whereby 2.482 g of a white solid were obtained (this means that 188.8 g of the solid are contained in the whole eluate).

Chlorine in the white solid was quantitatively analyzed. As a result, the content of chlorine was 0.01 wt. % or lower, indicating that ion exchange was effected almost completely. Further, the results of a mass spectroscopic analysis and elemental analysis of the white solid and $^1$H-NMR and $^{31}$P-NMR analyses of the white solid in the form of a solution in deuterated dimethyl sulfoxide were in full conformity with the corresponding data of a standard product of tetrakis[tris(dimethylamino)phosphoranylideneamino]phosphonium hydroxide.

The yield of the tetrakis[tris(dimethylamino)phosphoranylideneamino]phosphonium hydroxide was 94.7% based on the [tris(dimethylamino)phosphonioamino]tris[tris(dimethylamino)phosphoranylideneamino]phosphonium dichloride, so that highly-efficient ion exchange was successfully performed.

EXAMPLE 15

An aqueous solution of tetrakis[tris(dimethylamino)phosphoranylideneamino]phosphonium hydroxide was obtained in a similar manner as in Example 14. From the whole aqueous solution, water was distilled out at 60° C. under reduced pressure of 50 to 100 mmHg, whereby a white solid was obtained. The pressure was reduced further below 1 mmHg, at which the solid was dried at 60° C. for 5 hours. Tetrakis[tris(dimethylamino)phosphoranylideneamino]phosphonium hydroxide (188.5 g) was obtained as a solid.

EXAMPLE 16

An organic phase and a water phase were separated from each other after addition of aqueous hydrogen chloride solution in exactly the same manner as in Example 12, whereby 1,132.0 g of an aqueous solution containing 214.0 g (0.2636 mol) of [tris(dimethylamino)phosphonioamino]tris[tris(dimethylamino)phosphoranylideneamino]phosphonium dichloride were obtained. This aqueous solution contained the dichloride at a concentration of 18.9 wt. %.

It was concentrated into a 25.7 wt. % aqueous solution. To the entire amount of this aqueous solution, 263.6 ml of a 1 N aqueous solution of sodium hydroxide (factor: 1.000) (sodium hydroxide: 0.2636 mol) were added gradually. Soon after the initiation of the addition of the aqueous solution of sodium hydroxide, a white solid precipitated.

The solid was collected by filtration and washed twice with 75.0 g of water. When the white solid collected by filtration was dried under reduced pressure, its weight was 163.8 g. The results of a mass spectroscopic analysis, elemental analysis and chlorine analysis of the white solid and $^1$H-NMR and $^{31}$P-NMR analyses of the white solid in the form of a solution in deuterated dimethyl sulfoxide were in full conformity with the corresponding data of a standard product of tetrakis[tris(dimethylamino)phosphoranylideneamino]phosphonium chloride.

As has been described above, it was possible to regenerate and isolate tetrakis[tris(dimethylamino)phosphoranylideneamino]phosphonium chloride from the aqueous solution of [tris(dimethylamino)phosphonioamino]tris[tris(dimethylamino)phosphoranylideneamino]phosphonium dichloride.

The yield of the tetrakis[tris(dimethylamino)phosphoranylideneamino]phosphonium chloride was 80.2% based on the [tris(dimethylamino)phosphonioamino]tris[tris(dimethylamino)phosphoranylideneamino]phosphonium dichloride.

TABLE 1

| | Solvent | | Dichloride* | |
|---|---|---|---|---|
| Ex. | Kind | Amount, g | Weight, g | Yield, % |
| 5 | o-Dichlorobenzene | 38.0 | 9.55 | 98.1 |
| 6 | Toluene | 25.2 | 9.51 | 97.7 |
| 7 | Chlorobenzene | 32.2 | 9.50 | 97.6 |
| 8 | 2-Chlorotoluene | 31.5 | 9.50 | 97.6 |
| 9 | Anisole | 29.0 | 9.48 | 97.4 |

TABLE 1-continued

| | Solvent | | Dichloride* | |
|---|---|---|---|---|
| Ex. | Kind | Amount, g | Weight, g | Yield, % |
| 10 | Cyclohexane | 22.7 | 9.53 | 97.8 |
| 11 | Benzene | 25.8 | 9.51 | 97.7 |

*Dichloride: [Tris(dimethylamino)phosphonioamino]tris[tris-(dimethylamino)phosphoranylideneamino]-phosphonium dichloride According to the present invention, [tris(dimethylamino)phosphonioamino]tris[tris(dimethylamino)phosphoranylideneamino]phosphonium dichloride represented by the formula (1) can be used as a raw material for providing tetrakis[tris(dimethylamino)phosphoranylideneamino]phosphonium hydroxide in an extremely convenient manner upon preparation of the hydroxide important as a polymerization catalyst for alkylene oxides.

Further, this compound can be conveniently prepared from tetrakis[tris(dimethylamino)phosphoranylideneamino]phosphonium chloride and hydrogen chloride.

In addition, tetrakis[tris(dimethylamino)phosphoranylideneamino]phosphonium chloride can be conveniently transferred as [tris(dimethylamino)phosphonioamino]tris[tris(dimethylamino)phosphoranylideneamino]phosphonium dichloride from its solution in an organic solvent into a water phase, thereby making it possible to extract and separate the chloride. Further, tetrakis[tris(dimethylamino)phosphoranylideneamino]phosphonium hydroxide can be prepared conveniently and easily from the resulting aqueous solution of the dichloride.

Moreover, tetrakis[tris(dimethylamino)phosphoranylideneamino]phosphonium chloride can be easily regenerated and isolated from the aqueous solution of the dichloride.

We claim:

1. [Tris(dimethylamino)phosphonioamino]tris[tris(dimethylamino)phosphoranylideneamino]phosphonium dichloride represented by the following formula (1):

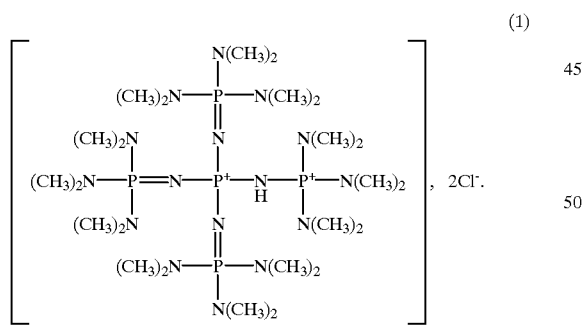

2. A process for preparing [tris(dimethylamino)phosphonioamino]tris[tris(dimethylamino)phosphoranylideneamino]phosphonium dichloride, which comprises:
bringing hydrogen chloride into contact with tetrakis[tris(dimethylamino)phosphoranylideneamino]phosphonium chloride, whereby said hydrogen chloride is added on said tetrakis[tris(dimethylamino)phosphoranylideneamino]phosphonium chloride.

3. A process according to claim 2, wherein said tetrakis[tris(dimethylamino)phosphoranylideneamino]phosphonium chloride is in the form of a solution in a substantially water-immiscible organic solvent and said hydrogen chloride is in the form of an aqueous solution of hydrogen chloride.

4. A process for separating tetrakis[tris(dimethylamino)phosphoranylideneamino]phosphonium chloride from a feed solution containing at least said tetrakis[tris(dimethylamino)phosphoranylideneamino]phosphonium chloride and a substantially water-immiscible organic solvent, which comprises:
adding an aqueous solution of hydrogen chloride to said feed solution either after washing said feed solution with water or without washing the same, whereby said tetrakis[tris(dimethylamino)phosphoranylideneamino]phosphonium chloride is extracted out in a water phase as [tris(dimethylamino)phosphonioamino]tris[tris(dimethylamino)phosphoranylideneamino]phosphonium dichloride which is a hydrogen chloride addition compound of said chloride.

5. A process for preparing tetrakis[tris(dimethylamino)phosphoranylideneamino]phosphonium hydroxide, which comprises:
adding an aqueous solution of hydrogen chloride to a feed solution, which contains at least said tetrakis[tris(dimethylamino)phosphoranylideneamino]phosphonium chloride and a substantially water-immiscible organic solvent, either after washing said feed solution with water or without washing the same, whereby said tetrakis[tris(dimethylamino)phosphoranylideneamino]phosphonium chloride is extracted out in a water phase as [tris(dimethylamino)phosphonioamino]tris[tris(dimethylamino)phosphoranylideneamino]phosphonium dichloride which is a hydrogen chloride addition compound of said chloride; and then
bringing the resulting aqueous solution of said [tris(dimethylamino)phosphonioamino]tris[tris(dimethylamino)phosphoranylideneamino]phosphonium dichloride into contact with an OH⁻-form ion exchange resin.

6. A process for isolating tetrakis[tris(dimethylamino)phosphoranylideneamino]phosphonium hydroxide, which comprises:
adding an aqueous solution of hydrogen chloride to a feed solution, which contains at least said tetrakis[tris(dimethylamino)phosphoranylideneamino]phosphonium chloride and a substantially water-immiscible organic solvent, either after washing said feed solution with water or without washing the same, whereby said tetrakis[tris(dimethylamino)phosphoranylideneamino]phosphonium chloride is extracted out in a water phase as [tris(dimethylamino)phosphonioamino]tris[tris(dimethylamino)phosphoranylideneamino]phosphonium dichloride which is a hydrogen chloride addition compound of said chloride;
bringing the resulting aqueous solution of said [tris(dimethylamino)phosphonioamino]tris[tris(dimethylamino)phosphoranylideneamino]phosphonium dichloride into contact with an OH⁻-form ion exchange resin, whereby an aqueous solution of tetrakis[tris(dimethylamino)phosphoranylideneamino]phosphonium hydroxide is obtained; and then
distilling off water under reduced pressure at a temperature not higher than 80° C. from said aqueous solution of said hydroxide, whereby said tetrakis[tris (dimethylamino)phosphoranylideneamino] phosphonium hydroxide is formed into a solid.

7. A process for isolating tetrakis[tris(dimethylamino) phosphoranylideneamino]phosphonium chloride, which comprises:

adding an aqueous solution of hydrogen chloride to a feed solution, which contains at least said tetrakis[tris (dimethylamino)phosphoranylideneamino] phosphonium chloride and a substantially water-immiscible organic solvent, either after washing said feed solution with water or without washing the same, whereby said tetrakis[tris(dimethylamino) phosphoranylideneamino]phosphonium chloride is extracted out in a water phase as [tris(dimethylamino) phosphonioamino]tris[tris(dimethylamino) phosphoranylideneamino]phosphonium dichloride which is a hydrogen chloride addition compound of said chloride; and then neutralizing with the hydroxide of an alkali metal or alkaline earth metal the resulting aqueous solution of said [tris(dimethylamino)phosphonioamino]tris[tris (dimethylamino)phosphoranylideneamino] phosphonium dichloride either as is or after concentration, whereby said tetrakis[tris (dimethylamino)phosphoranylideneamino] phosphonium chloride is regenerated and precipitated as a solid from said aqueous solution of said dichloride.

8. A process according to claim 7, wherein said substantially water-immiscible organic solvent is an organic solvent selected from saturated aliphatic hydrocarbons having 6–8 carbon atoms, benzene, alkyl-substituted aromatic hydrocarbons having 7–9 carbon atoms, chlorinated benzenes having 1–3 chlorine atoms, chlorinated and alkyl-substituted aromatic hydrocarbons having 7–9 carbon atoms and 1–2 chlorine atoms, and ethers having 4–8 carbon atoms.

9. A process according to claim 8, wherein said feed solution is a solution available by removing solid aminotris (dimethylamino)phosphonium chloride from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a by-product in said reaction.

10. A process according to claim 8, wherein said feed solution is a solution available by removing solid aminotris (dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino) phosphoranylideneamino]phosphonium chloride, said solid aminotris(dimethylamino)phosphonium chloride being a by-product in said reaction.

11. A process according to claim 6, wherein said substantially water-immiscible organic solvent is an organic solvent selected from saturated aliphatic hydrocarbons having 6–8 carbon atoms, benzene, alkyl-substituted aromatic hydrocarbons having 7–9 carbon atoms, chlorinated benzenes having 1–3 chlorine atoms, chlorinated and alkyl-substituted aromatic hydrocarbons having 7–9 carbon atoms and 1–2 chlorine atoms, and ethers having 4–8 carbon atoms.

12. A process according to claim 5, wherein said substantially water-immiscible organic solvent is an organic solvent selected from saturated aliphatic hydrocarbons having 6–8 carbon atoms, benzene, alkyl-substituted aromatic hydrocarbons having 7–9 carbon atoms, chlorinated benzenes having 1–3 chlorine atoms, chlorinated and alkyl-substituted aromatic hydrocarbons having 7–9 carbon atoms and 1–2 chlorine atoms, and ethers having 4–8 carbon atoms.

13. A process according to claim 4, wherein said substantially water-immiscible organic solvent is an organic solvent selected from saturated aliphatic hydrocarbons having 6–8 carbon atoms, benzene, alkyl-substituted aromatic hydrocarbons having 7–9 carbon atoms, chlorinated benzenes having 1–3 chlorine atoms, chlorinated and alkyl-substituted aromatic hydrocarbons having 7–9 carbon atoms and 1–2 chlorine atoms, and ethers having 4–8 carbon atoms.

14. A process according to claim 3, wherein said substantially water-immiscible organic solvent is an organic solvent selected from saturated aliphatic hydrocarbons having 6–8 carbon atoms, benzene, alkyl-substituted aromatic hydrocarbons having 7–9 carbon atoms, chlorinated benzenes having 1–3 chlorine atoms, chlorinated and alkyl-substituted aromatic hydrocarbons having 7–9 carbon atoms and 1–2 chlorine atoms, and ethers having 4–8 carbon atoms.

15. A process according to claim 7, wherein said feed solution is a solution available by removing solid aminotris (dimethylamino)phosphonium chloride from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a byproduct in said reaction.

16. A process according to claim 6, wherein said feed solution is a solution available by removing solid aminotris (dimethylamino)phosphonium chloride from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a byproduct in said reaction.

17. A process according to claim 5, wherein said feed solution is a solution available by removing solid aminotris (dimethylamino)phosphonium chloride from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a byproduct in said reaction.

18. A process according to claim 4, wherein said feed solution is a solution available by removing solid aminotris (dimethylamino)phosphonium chloride from a reaction mixture obtained by reacting phosphorus pentachloride with iminotris(dimethylamino)phosphorane and containing tetrakis[tris(dimethylamino)phosphoranylideneamino] phosphonium chloride, said solid aminotris(dimethylamino) phosphonium chloride being a byproduct in said reaction.

19. A process according to claim 7, wherein said feed solution is a solution available by removing solid aminotris (dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino) phosphoranylideneamino]phosphonium chloride, said solid aminotris(dimethylamino)phosphonium chloride being a byproduct in said reaction.

20. A process according to claim 6, wherein said feed solution is a solution available by removing solid aminotris (dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino) phosphoranylideneamino]phosphonium chloride, said solid aminotris(dimethylamino)phosphonium chloride being a byproduct in said reaction.

21. A process according to claim 5, wherein said feed solution is a solution available by removing solid aminotris (dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino) phosphoranylideneamino]phosphonium chloride, said solid aminotris(dimethylamino)phosphonium chloride being a byproduct in said reaction.

22. A process according to claim 4, wherein said feed solution is a solution available by removing solid aminotris (dimethylamino)phosphonium chloride from a reaction mixture obtained by reacting phosphorus pentachloride with iminotris(dimethylamino)phosphorane at a molar ratio of from 1:7.00 to 1:12.00 at 10 to 90° C. in an initial stage of said reaction and then at 110 to 200° C. in an aromatic hydrocarbon or halogenated aromatic hydrocarbon as a solvent and containing tetrakis[tris(dimethylamino) phosphoranylideneamino]phosphonium chloride, said solid aminotris(dimethylamino)phosphonium chloride being a byproduct in said reaction.

\* \* \* \* \*